(12) United States Patent
Florexil (10) Patent No.: US 11,439,768 B2
(45) Date of Patent: Sep. 13, 2022

(54) COMPARTMENTALIZED SYRINGE FOR COMBINED MEDICINE AND FLUSH SOLUTION

(71) Applicant: Wagner Florexil, Riverview, FL (US)

(72) Inventor: Wagner Florexil, Riverview, FL (US)

( * ) Notice: Subject to any disclaimer, the term of this patent is extended or adjusted under 35 U.S.C. 154(b) by 159 days.

(21) Appl. No.: 16/931,323

(22) Filed: Jul. 16, 2020

(65) Prior Publication Data

US 2021/0016010 A1 Jan. 21, 2021

Related U.S. Application Data

(60) Provisional application No. 62/875,000, filed on Jul. 17, 2019.

(51) Int. Cl.
| | | |
|---|---|---|
| *A61M 5/31* | (2006.01) | |
| *A61M 5/315* | (2006.01) | |
| *A61M 5/14* | (2006.01) | |
| *A61M 5/178* | (2006.01) | |

(52) U.S. Cl.
CPC ........ *A61M 5/3158* (2013.01); *A61M 5/3129* (2013.01); *A61M 5/31513* (2013.01); *A61M 2005/1403* (2013.01); *A61M 2005/1787* (2013.01); *A61M 2005/3131* (2013.01)

(58) Field of Classification Search
CPC ............ A61M 2005/1787; A61M 5/19; A61M 5/284; A61M 5/31596; A61M 5/3294; A61M 5/244; A61M 2005/31598; A61M 2005/3128
See application file for complete search history.

(56) References Cited

U.S. PATENT DOCUMENTS

| | | | | |
|---|---|---|---|---|
| 2,888,923 A * | 6/1959 | Da Cunha | ......... | A61M 5/31596 604/224 |
| 3,735,761 A * | 5/1973 | Hurschman | ............. | A61M 5/32 604/196 |
| 3,977,402 A * | 8/1976 | Pike | ........................ | A61M 5/24 604/511 |
| 4,036,225 A * | 7/1977 | Maury | .............. | A61M 5/31596 604/88 |
| 5,032,117 A * | 7/1991 | Motta | ................. | A61M 5/31511 604/218 |
| 5,330,426 A * | 7/1994 | Kriesel | ................ | A61M 5/2429 604/82 |
| 5,637,087 A * | 6/1997 | O'Neil | ................... | A61M 5/284 604/82 |
| 5,865,798 A * | 2/1999 | Grimard | ........... | A61M 5/31596 604/218 |
| 6,349,850 B1 * | 2/2002 | Cheikh | ................. | A61J 1/2096 222/1 |

(Continued)

*Primary Examiner* — William R Carpenter
(74) *Attorney, Agent, or Firm* — Tiffany C. Miller; Inventions International Inc.

(57) ABSTRACT

A compartmentalized syringe configured to retain both the medicine and the flushing solution in the same housing. At least one smaller fluid or solid containing container will be added inside the flush housing and will separate its content(s) from other fluids or solids inside the flush housing. The shape of the housing and inner containers can be similar with the outer syringe flush with channels to facilitate the flow of fluids and they can also be of different shapes which will automatically create channels to allow the flow of fluid. An opening in the syringe plunger configured to receive a medicine vial.

18 Claims, 8 Drawing Sheets

(56) References Cited

U.S. PATENT DOCUMENTS

| | | | | |
|---|---|---|---|---|
| 6,558,358 B2 * | 5/2003 | Rosoff | ............... | A61M 5/282 |
| | | | | 604/200 |
| 7,850,663 B2 * | 12/2010 | Sullivan | ............ | A61M 15/0028 |
| | | | | 604/87 |
| 8,814,823 B2 * | 8/2014 | Pickhard | ............... | A61M 5/284 |
| | | | | 604/82 |
| 9,283,313 B2 * | 3/2016 | Huemer | ............... | G01N 33/491 |
| 2008/0171971 A1 * | 7/2008 | DiPerna | ............ | A61M 5/31596 |
| | | | | 604/82 |
| 2012/0136316 A1 * | 5/2012 | Davies | ............... | A61M 5/3294 |
| | | | | 604/191 |
| 2013/0030412 A1 * | 1/2013 | Bartlett, II | .......... | A61M 5/2448 |
| | | | | 604/87 |
| 2016/0296703 A1 * | 10/2016 | Bailey | ............... | A61M 5/285 |

\* cited by examiner

COMPARTMENTALIZED SYRINGE FOR COMBINED MEDICINE AND FLUSH SOLUTION

CROSS REFERENCE TO RELATED APPLICATIONS

This application is a Non-Provisional Utility application entitled, "Compartmentalized Syringe for Combined Medicine and Flush Solution", which claims priority to U.S. Provisional Patent Application No. 62/875,000, filed Jul. 17, 2019, entitled, "Easier, Better Syringe Flush".

BACKGROUND OF THE INVENTION

1. Field of the Invention

This innovation relates, generally, to a medical syringe. More particularly, it relates to a compartmentalized syringe capable of retaining and/or delivering both a medicine and flush solution. Further, medicines may be loaded into a compartment of a syringe without using an exterior needle.

2. Background Art

Syringe flush is used quite often in healthcare delivery. One of its main uses is to deliver intravenous medicines. Intravenous flush syringes are common medical devices used to clear intravenous lines. After a medicine is delivered, the need to flush residual medication with solution such as a saline solution is critical in preventing incompatibility issues between them and or keeping the integrity of the individual medications. This need to flush residual medication from the line is important especially since most medications are clear and colorless. Currently, a medical professional administers a first drug with a first syringe and is then required to perform a second step with a second syringe containing the flush solution. Unfortunately, some medical professionals might forget to perform this second step or be too overburdened and skip this second flushing step. In the situation were medical supplies may be limited, the second syringe may not be available for performing the flushing step. It would be more desirable to eliminate the need for a separate syringe containing the flush solution, thereby, eliminating the need for additional medical supplies which would eliminate associated costs. The ability to flush medicine after delivery using the same syringe instead of two syringes is more convenient. Thus, there is a need for a novel syringe having a compartment retaining both the medicine and the flush solution.

Further, the convenience of loading some medicines in the syringe with or without using a needle and the attachment of alcohol configured to clean the connector before attaching the syringe will help medical professionals reduce needle stick injuries and decrease medicine delivery time. It would be more desirable to load medicines using either the novel modification made in the plunger to house medical vials or the syringe hub (tip) to help reduce the medicine loading time, increase compliance when it comes to flushing after medicine delivery, reduce drug interaction, and reduce costs.

It is within the scope of this current invention for a syringe to flush the intravenous line after delivering a medication without the need to use a subsequent syringe containing the flush solution. The ability to use certain types of medicine vials by loading them through the modified plunger without using needles to extract the medicine and the capability of some medications being pre-loaded is another advantage of this innovation. As a result, potential nesting material for microorganisms associated with not flushing medicine after delivery might be reduced and or eliminated and the risk of catheter-related bloodstream infection may be reduced and or eliminated as well.

However, in view of the prior art considered as a whole at the time the present invention was made, it was not obvious to those of ordinary skill in the pertinent art how the identified needs could be fulfilled.

SUMMARY OF THE INVENTION

The long-standing but heretofore unfulfilled need for a compartmentalized syringe configured to retain both the medicine and the flushing solution in the same housing. At least one smaller fluid or solid containing container will be added inside the flush housing and will separate its content(s) from other fluids or solids inside the flush housing. The shape of the housing and inner containers can be similar with the outer syringe flush with channels to facilitate the flow of fluids and they can also be of different shapes which will automatically create channels to allow the flow of fluid. An opening in the syringe plunger is configured to receive a medicine vial, and which also includes improvements that overcome the limitations of prior art syringe components is now met by a new, useful, and non-obvious invention.

Provided is a preferred embodiment of a plunger of a syringe having a first piercing element configured to puncture a separate fluid filled container within the barrel of the syringe. The barrel also contains another fluid for mixing with medication and is not in contact with the fluid.

In another embodiment, medicines can be mixed inside the container for delivery while the fluid filled container inside the barrel remains untouched until it is pierced by a sharp edge design to puncture the container and release its content toward the end of the syringe during medication administration for flushing. The container located within the barrel of the syringe may retain one or more medicines in one or more compartments. The container may contain solution for mixing separated from the medicine which could be preloaded, separated but ready for reconstruction at the point of delivery which will preserve the pharmacokinetics and pharmacodynamics. It is within the scope of this current invention for the syringe to have both medicine and mixing solution within containers, the medicine alone inside a container while the solution for mixing is inside the syringe barrel, or the solution for mixing with medicine in the container alone while the medicine is in the barrel. The sharp point of the piercing element is configured to puncture the container which can also be used to release and mix medicine with mixing solution or a push or pull mechanism can be used.

In yet another embodiment the novel syringe flush could also have a modified plunger design to load a plurality of differing sized medical vials. A sharp end design to puncture medical vials design to fit and which will reduce the need to use needles and potential needle stick injury they may cause. The innovative plunger will be more convenient when it comes to loading medicines inside the syringe barrel without using needles. Further, at least one opening in the syringe plunger is configured to retain an attachment including, but not limited to, medicine vials and/or alcohol preparation pads.

The syringe flush is configured to deliver both medicines and flush using a single all in one syringe flush having a separate inner fluid filled container. The inner fluid filled container has a collapsible feature design for flushing after medicine delivery without the need to use a second flush. The inner container design has at least one channel designed to allow fluid to flow in and out of the syringe flush barrel. The inner container can take any shape that can create passages for fluid between the walls of the syringe flush barrel and the container for flush. The syringe flush can deliver both medicines and flush using a single all in one syringe flush having a separate inner fluid filled container. A sharp point design for piercing the collapsible container and release its content for flush. The modified plunger of the syringe flush may have an opening design to house medicine vials. The plunger of the syringe flush has a drug vial adaptor designed to pierce and allow medicine delivery to the syringe barrel. The modified plunger of the syringe flush can have a conduit design to convey fluid and or air and medicine to either side. The syringe for flush has the capability to load medicine from either end of the apparatus. One end of the syringe for flush has the lure lock where needles can be attached to mix and extract medicines, especially in larger vials. Another end has the newly redesign plunger designed to accommodate medicine vials.

The novel syringe has a plunger having a shaft. The shaft of the plunger has a flange located opposite a sealing structure. The sealing structure has a first side located opposite a second side. The first side of the sealing structure has a first piercing element. The second side of the sealing structure is connected to the shaft of the plunger. The syringe has barrel having a chamber receiving the sealing structure of the plunger. The syringe has a first container retaining a substance. The first container is configured to be punctured by a first piercing element when a user depresses the plunger within the barrel of the syringe.

In an alternate embodiment, the syringe has a first container being collapsible. The first container can have at least one channel located on an outer wall surface of the first container.

In an alternate embodiment, the syringe has a plunger having at least one recess retaining an alcohol pad. At least one recess of the plunger has a removable lid.

In an alternate embodiment, the syringe has a barrel of the syringe retaining a second container. The second container containing a substance. The second container is configured to be punctured by the first piercing element when a user depresses said plunger within the barrel of the syringe.

In an alternate embodiment, the syringe has a shaft of the plunger having a loading chamber. The loading chamber receives a vessel retaining a substance. The loading chamber of the plunger has an inner wall surface having at least one protruding structure. At least one protruding structure is configured to engage the vessel and secure the vessel within the loading chamber.

In an alternate embodiment, the second side of the sealing structure has at least one support structure such as a plurality of ribs configured to engage a plurality of differing sized vessels and secure the vessels within the loading chamber of the plunger.

In an alternate embodiment, the second side of the sealing structure has a second piercing element configured to puncture at least a portion of the vessel to release the substance from the vessel when a user depresses the vessel into the loading chamber of the plunger. The second piercing element has at least one opening connected to a rotating conduit. The rotating conduit slidably traverses through the sealing structure of the plunger to the barrel of the syringe. The conduit is configured to be oriented in a closed orientation to prevent the substance from flowing from the plunger to the barrel of the syringe. The rotatable conduit is configured to be oriented in an open orientation to allow the substance to flow from the plunger, through the sealing structure, and to the barrel of the syringe. The second piercing element can have at least one flange.

In an alternate embodiment, the sealing structure has a first cylindrical structure having a first bore and a second bore. The sealing structure has a second cylindrical structure having a third bore and a fourth bore. The second side of the sealing structure has a second piercing element. The second piercing element is configured to puncture at least a portion of the vessel to release the substance from the vessel when a user depresses the vessel into the loading chamber of the plunger. The second piercing element has at least one opening. The at least one opening of the second piercing element is connected to the first bore and the second bore of the first cylindrical structure. The first bore and the second bore of the first cylindrical structure are oriented in an open configuration to align with the third bore and the fourth bore of the second cylindrical structure to allow the substance to flow from the vessel of the plunger to the barrel of the syringe. The second piercing element can have at least one flange.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

Figure 1A:
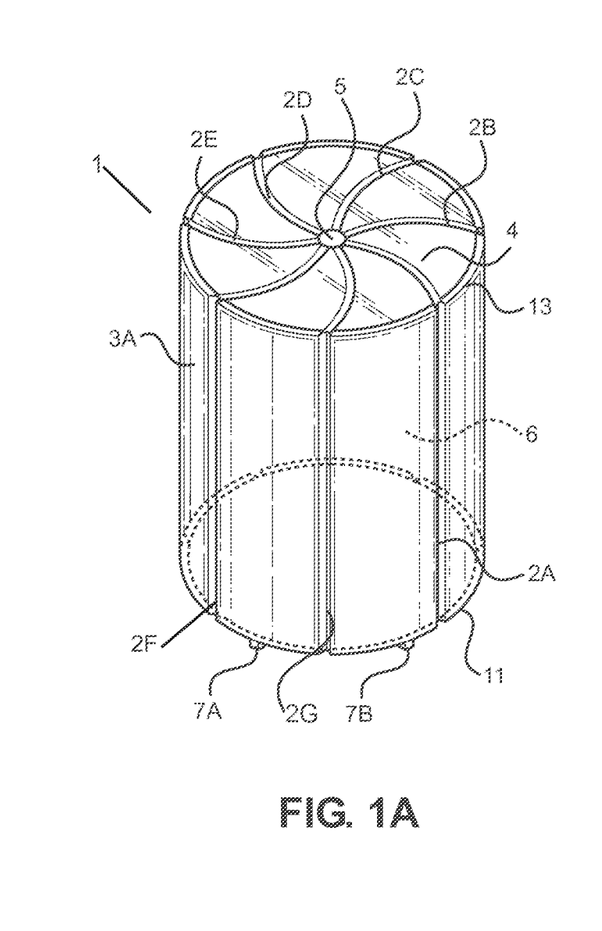
FIG. 1A is a sectional view of a first embodiment of the novel container having radiused edges with at least one channel on the side that will be placed inside the syringe and which will contain fluid for flushing the medicine after delivery.
Figure 1B:
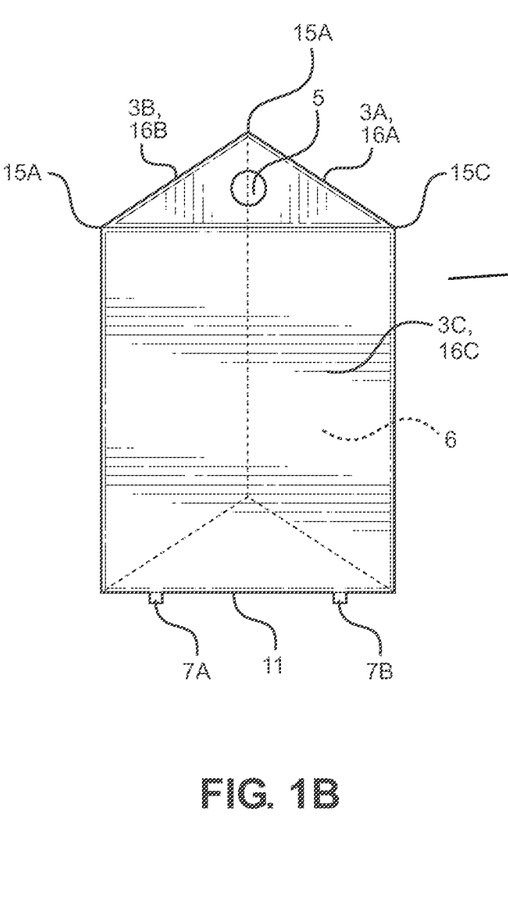
FIG. 1B is a sectional view of an alternate embodiment of the novel container having vertices with at least one channel on the side that will be placed inside the syringe and which will contain fluid for flushing the medicine after delivery.
Figure 2:
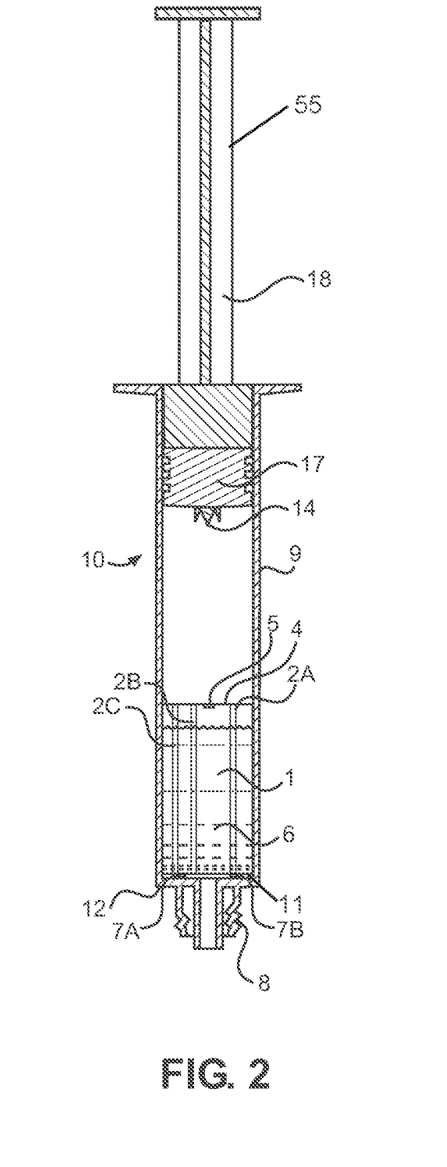
FIG. 2 is a side sectional view of a first embodiment of the novel fluid filled first collapsible container retained inside a syringe having at least a portion of the plunger seal with a piercing element having a sharp edge design configured to puncture the first collapsible container and release its content.
Figure 3:
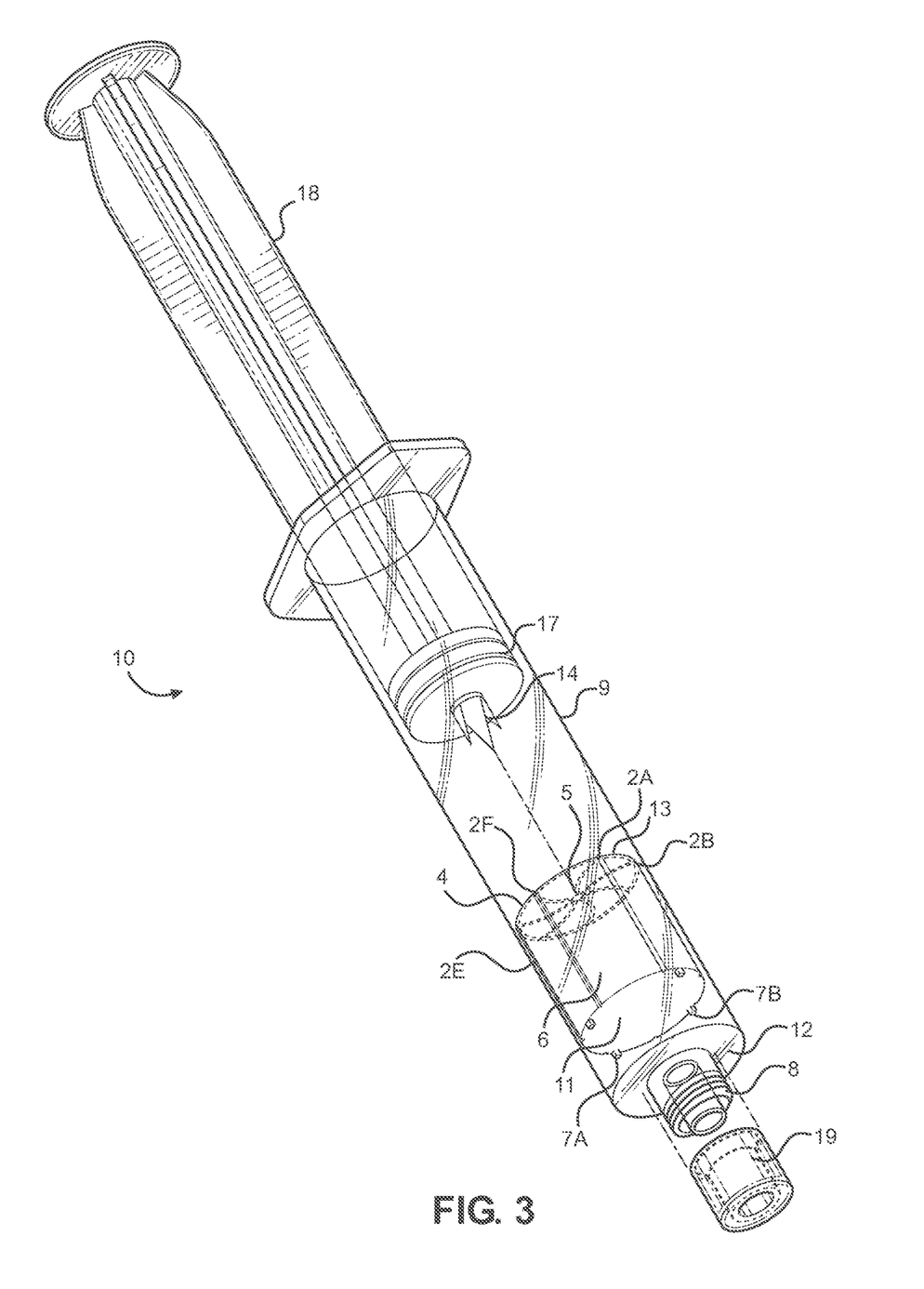
FIG. 3 is a perspective view of a first embodiment of the novel fluid filled first collapsible container retained inside the syringe having at least a portion of the plunger seal with a piercing element having a sharp edge design configured to puncture the first collapsible container and release its content.

FIGS. 1A, and 2-3 illustrate collapsible container 1 retaining fluid 6. It is within the scope of this invention for fluid 6 to be configured to flush the medicine after delivery. In a preferred embodiment container 1 may be collapsible, however, container 1 may not be collapsible. In a preferred embodiment, collapsible container 1 is designed to fit or float within the chamber of barrel 9 of syringe 10. The main function of collapsible container 1 is to be pierced, punctured, and/or ruptured by first piercing element 14 so that flush solution 6 retained within collapsible container 1 is released from collapsible container 1 and then expelled trough hub 8 of syringe 10. Collapsible container 1 has a plurality of channels 2A-2G (FIG. 1A) located on the bottom portion, top portion 4, and side wall portion 3 (FIG. 1B) to allow fluid 6 to flow out of collapsible container 1 for delivery through hub 8 (FIGS. 2 and 3) of syringe 10 (FIGS. 2 and 3) or for fluid 6 to be retained within barrel 9 (FIGS. 2 and 3) of syringe 10 (FIGS. 2 and 3). Bottom portion 11 of collapsible container 1 has at least one protrusion 7 or continuation of at least one of the channels 2A-2G as it prevents collapsible container 1 to go completely flush with bottom portion 12 of barrel 9 (FIGS. 2 and 3) of syringe 10 (FIGS. 2 and 3) and therefore allow the flow of fluid 6 in and out. Channels 2A-2G allow fluid to flow out of hub 8 for delivery or inside barrel 9. It is within the scope of this invention for the channels 2A-2G to continue to prevent the container from going completely flush with bottom 12 of barrel 9. FIGS. 1A and 2 show collapsible container having radiused edges 13. Top portion 4 of collapsible container 1 has contact surface 5 configured to receive first piercing element 14 (FIGS. 2 and 3). It is within the scope of this invention for the shape of container 1 to vary and may be radiused and/or have corners.

FIG. 1B shows collapsible container 1 having vertices 15A-15C which are corners and flat surfaces 16 whereby collapsible container 1 can have a plurality of sides 3A-3C. Channels can be created between barrel 9 (FIG. 2) of syringe 10 (FIG. 2) and side walls 3A-3C of collapsible container 1 when collapsible container 1 shape is non-circular such as triangular shaped, to allow a substance and/or a fluid to flow through syringe 10. It is within the scope of this invention for a substance to include, but not be limited to, a fluid, a liquid, a powder, a medicine, a flush solution, and/or saline solution. The same spacer and/or protrusion 7A and 7B seen in FIG. 1A is illustrated in FIG. 1B and protrusion 7A and 7B is configured to maintain the space between barrel 9 (FIG. 2) of syringe 10 (FIG. 2) and collapsible container 1, when collapsible container 1 is retained within barrel 9 (FIG. 2) of syringe 10 (FIG. 2) to allow the flow of fluid 6 in or out. It is within the scope of this invention for spacer and/or protrusion 7A and 7B to be replaced by channels which can be located on the barrel or on the bottom of the inner container.

Figure 4:
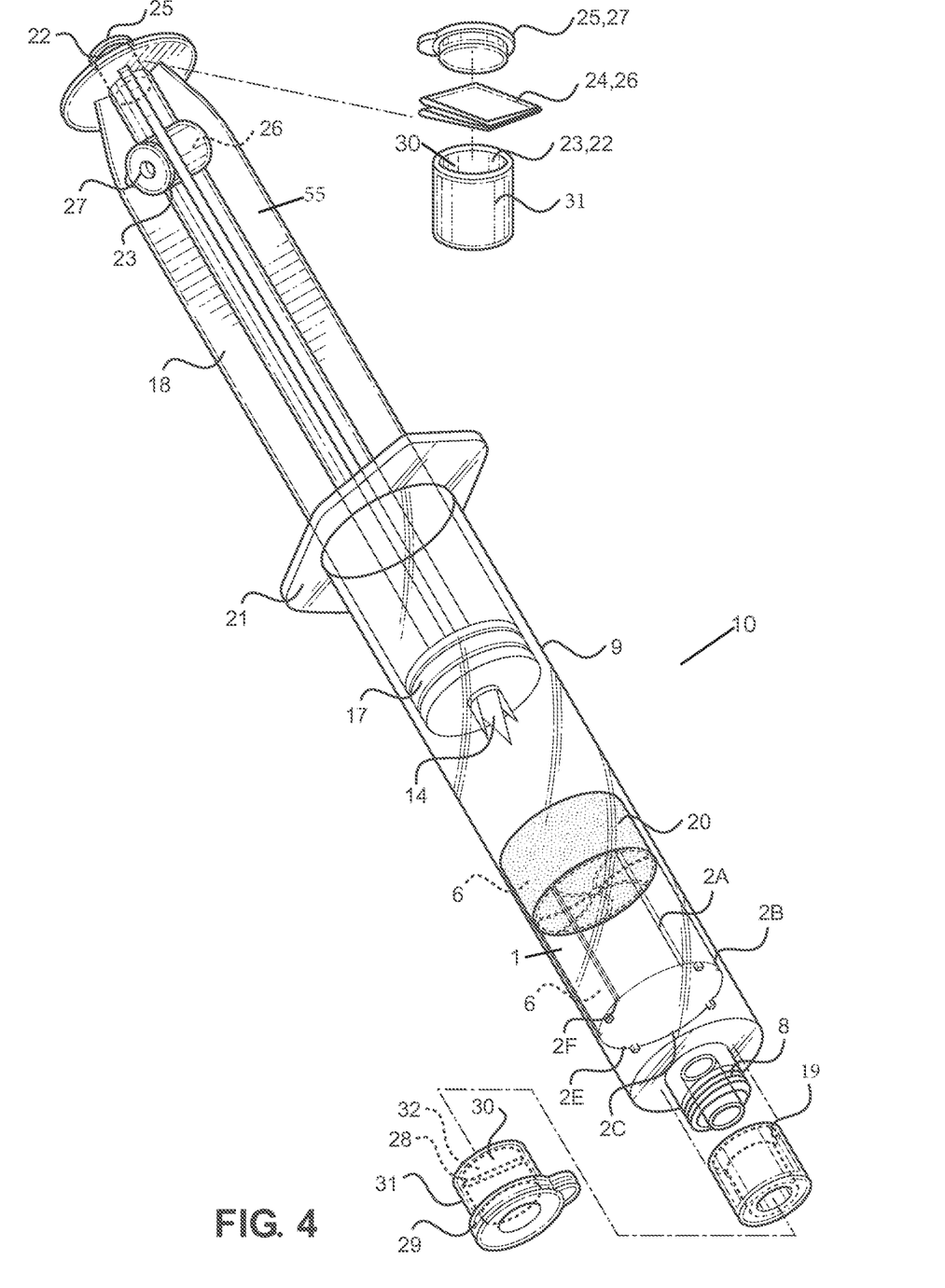
FIG. 4 is a perspective view of a second embodiment of the novel syringe of FIGS. 2 and 3 having a plunger with a compartment configured to retain an alcohol prep pad and the barrel retaining a first collapsible container and a second collapsible container.
Figure 5:
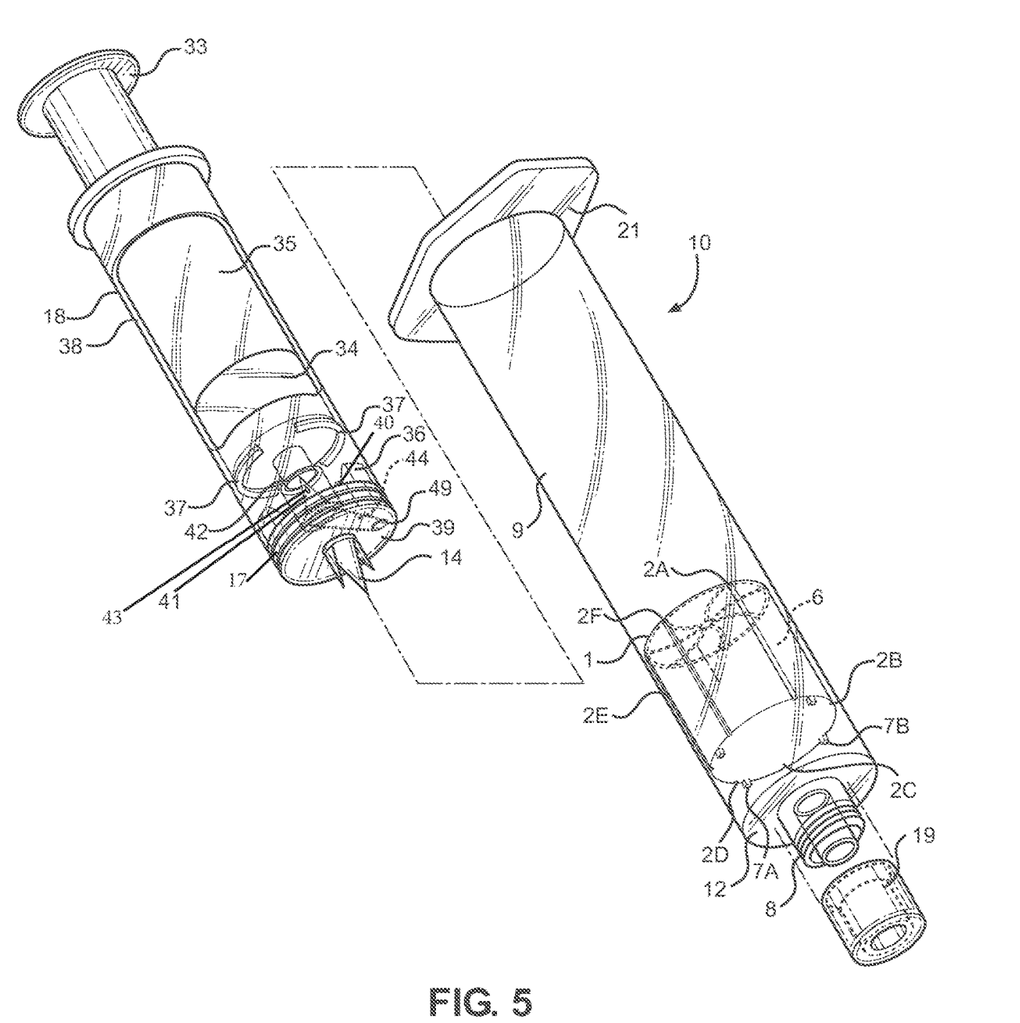
FIG. 5 is an exploded view of the third embodiment of the novel syringe having a plunger configured to retain and house a medicine vial, having a first piercing element and a second piercing element connected to both sides of the plunger seal, and a conduit that allows the transfer of the medicine from inside the medicine vial to the barrel of the syringe.

FIGS. 2, 3, and 5 depict first collapsible container 1 being retained inside barrel 9 of syringe 10. Collapsible container 1 retains fluid 6 that will be used for flushing. Hub 8 of syringe 10 is connected to bottom portion 12 of syringe 10 and hub 8 is configured to connect a variety of removable attachments including, but not limited to, a needle, an intravenous catheter, a tube, lid 19 (FIG. 3), and/or a drain. First piercing element 14 is a sharp object such as a needle or a razor connected to at least a portion of sealing structure 17 of plunger 18. First piercing element 14 is configured to pierce collapsible container 1 retained within barrel 9 of syringe 10 when a user depresses plunger 18. Plunger 18 has shaft 55. Shaft 55 has flange 33 located opposite sealing structure 17. It is also within the scope of this invention for first piercing element 14 to be located on the container itself. When first piercing element 14 is depressed by a user into contact surface 5 of collapsible container 1, the puncture releases fluid 6 content from collapsible container 1. Fluid 6 will then travel down at least one channel 2A-2F. Channels 2A-2F are recesses located on an outer wall surface of collapsible container 1 so that fluid 6 can traverse along channels 2A-2F toward hub 8 of syringe 10. It is within the scope of this invention for the sharp point for piercing can also be placed on the container itself. FIGS. 3-5 have lid 19 configured to cover hub 8.

FIG. 4 illustrates a second embodiment of the barrel 9 of syringe 10 retaining a plurality of collapsible containers being first collapsible container 1 and second collapsible container 20. It is within the scope of this invention for first container 1 and/or second container 20 to retain any solution 6 in liquid or powder form including, but not limited to, medicine, saline, and/or flush solution. Barrel 9 has flange 21. In an example, second collapsible container 20 retains pre-loaded medicine 6. First piercing element 14 is connected to sealing structure 17 located at an end on plunger 18. When plunger 18 is depressed by a user, first piercing element 14 contacts and pierces second collapsible container 20 so that pre-loaded medicine 6 is released from second collapsible container 20. The released medicine 6 flows through channels 2A-2F of first collapsible container 1 and exits syringe 10 through hub 8. Next, the user depresses plunger 18 even further so that second collapsible container 20 becomes deformed and collapses to a point to where first piercing element 14 is capable of piercing through first collapsible container 1. When first collapsible container 1 is pierced by first piercing element 14, flush solution 6 is released from first collapsible container 1 and travels along channels 2A-2F of first collapsible container 1 and exits syringe 10 through hub 8. It is within the scope of this invention for first collapsible container 1 and/or second collapsible container 20 to have a single or a plurality of compartments that may retain medicine in powder solid or liquid form and/or solution for mixing with other medicine.

Figure 6:
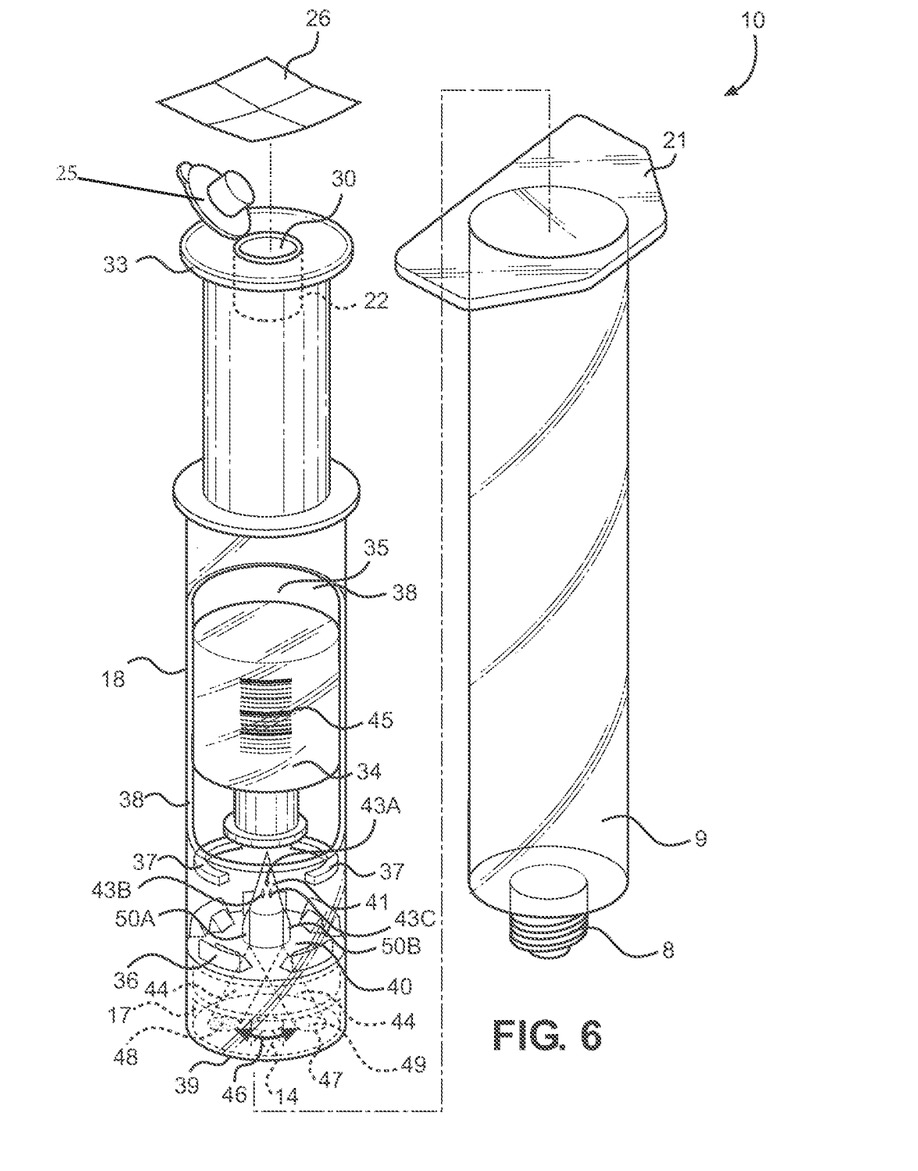
FIG. 6 is a side view of the third embodiment of the novel syringe having a plunger configured to retain and house a medicine vial, having a first piercing element and a second piercing element connected to both sides of the plunger seal, and a conduit that allows the transfer of the medicine from inside the medicine vial to the barrel of the syringe.

FIGS. 4 and 6 show a second embodiment of syringe 10 having shaft 55 or flange 33 of plunger 18 having at least one opening and/or recess 22 retaining alcohol and or/an alcohol pad. An integrated alcohol pad design allows a user to clean the connector which could also be located in one of the openings of the plunger. Plunger 18 has first recess 22 located on an end at flange 33 of plunger 18 located opposite sealing structure 17. First recess 22 of plunger retains alcohol pad 24. Because alcohol pad contours inner wall surface of first recess 22, chamber 30 forms. Alcohol pad 24 is made of a layer of material such as cotton having alcohol. Removable lid 25 is connected to first recess 22 so that alcohol 24 pad does not dry out. Plunger 18 has second recess 23 located on a side of plunger 18. Referring now to FIG. 4, second recess 23 of plunger 18 retains alcohol pad 26. Because alcohol pad 26 contours inner wall surface of second recess 23, chamber 30 forms. Alcohol pad 26 is made of a layer of material such as cotton having alcohol. It is within the scope of this invention for the alcohol pad to be connected to the inner wall surface of the recess, forming an alcohol pad chamber 30. Chamber 30 is configured to receive an end of an attachment such as, a connector, for cleaning prior to use. When an attachment is installed into chamber 30 during cleaning, the alcohol pad is located on the end and all sides of the attachment for a thorough cleaning. Removable lid 27 is connected to second opening 23 so that alcohol 26 pad does not dry out. Lid 19 of hub 8 can have vessel 31 connected thereto. Vessel 31 has third recess 32 retaining alcohol pad 28. Because alcohol pad 28 contours inner wall surface of third recess 32 of vessel 31, chamber 30 forms. Removable lid/cover 29 covers vessel 31. Vessel 31 can be retained within an opening of plunger 18 when not in use. It is within the scope of this current invention for the alcohol pad and/or vessel 31 retaining alcohol pad 30 to be located at the lid 19 of hub 8, within the shaft of plunger 18, at plunger flange 33. In a preferred embodiment at least one alcohol is needed, however, it is within the scope of this invention for a plurality of alcohol pads to be retained within syringe 10.

Figures 7, 8:
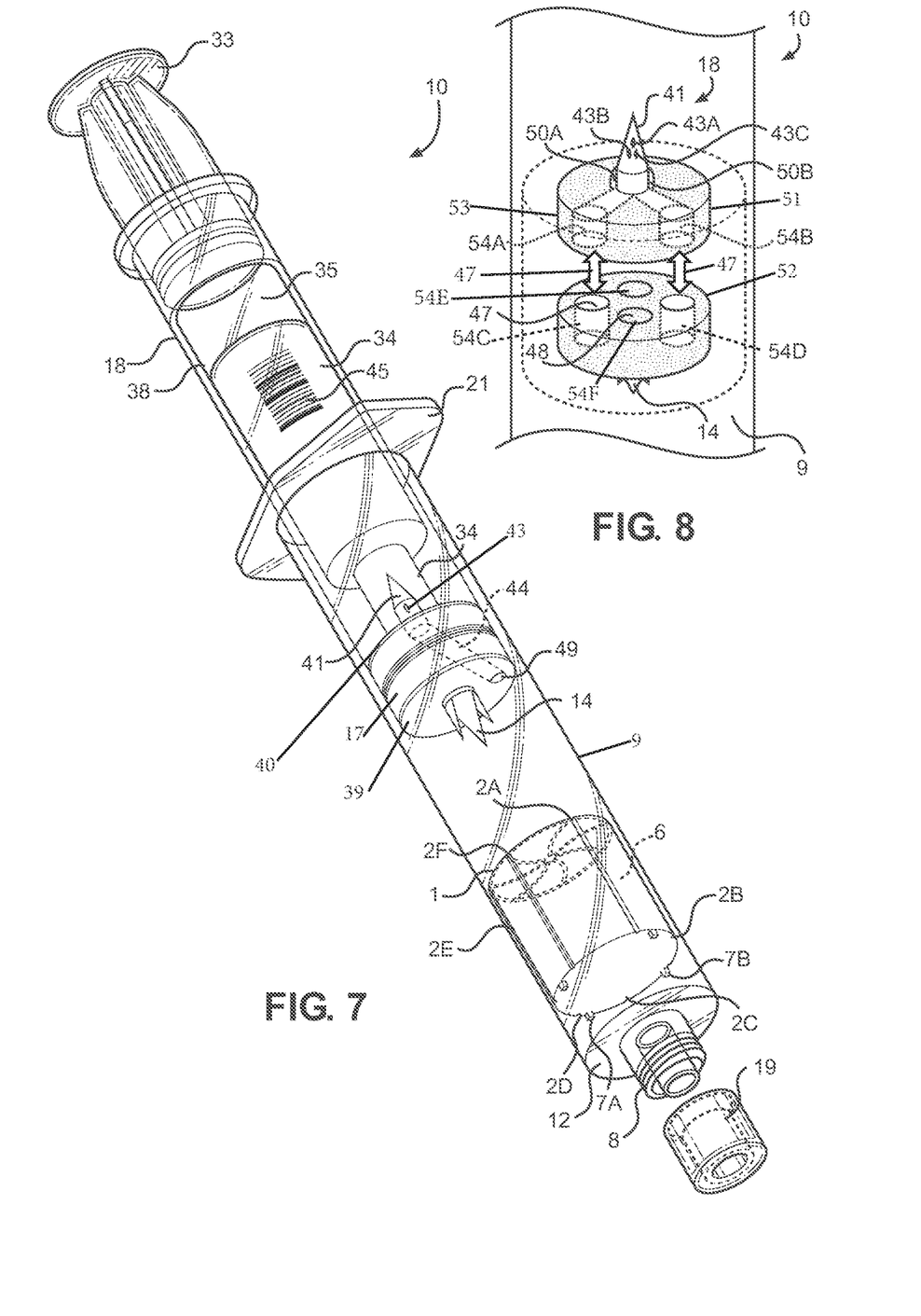
FIG. 7 is a perspective view of the third embodiment of the novel syringe having a plunger configured to retain and house a medicine vial, having a first piercing element and a second piercing element connected to both sides of the plunger seal, and a conduit that allows the transfer of the medicine from inside the medicine vial to the barrel of the syringe.
FIG. 8 is a perspective view of a fourth alternate embodiment of the third embodiment having a sealing structure with two cylindrical structures that are configured to be oriented to align with each other to facilitate flow of fluid from the plunger to the barrel of a syringe; and, FIG. 9 is an exploded view of a fifth embodiment of the novel syringe of FIG. 4 having a syringe with a first barrel and a second barrel having a container retaining a solution with a flange, a first wing, and a second wing.

FIGS. 5-7 illustrates a third embodiment of syringe 10 having plunger 18 having loading chamber 35 having inner wall surface 38 configured to house at least one medical vial 34. It is within the scope of the innovation that container 1 with the flushing solution 6 and the sharp point 14 configured to pierce container 1 can be relocated. For example, container 1 with fluid 6 for flushing can be relocated closer to plunger sealing structure 17 while sharp point 14 for piercing could be placed closer to hub 8 of syringe 10. Barrel 9 of syringe 10 retains container 1 containing fluid 6 that will be used for flushing. In a preferred embodiment, loading chamber 35 accommodates at least one vessel such as a medicine vial 34, a bottle, a vial, and/or a container which could help reduce the use of needles at the hub 9 of syringe 10 and potentially reduce needle stick injuries. An inner wall surface 38 of loading chamber 35 has protruding structure 37 serving as a locking mechanism configured to secure medicine vial 34 in place.

FIGS. 5-7 show sealing structure 17 having first side 39 having first piercing element 14 located opposite second side 40 of sealing structure 17 having a second piercing element 41. Second side 40 of sealing structure 17 may have a plurality of support structures 36 and/or ribs configured to secure medicine vial 34 in place. Support structures 36 can be oriented in a circular pattern in subsequent rows to accommodate differing sized diameter vials. The sharp end 41 is configured to pierce medicine vials 34. Second piercing element 41 may be covered with removable lid 42 to protect piercing element 41 from environmental exposures including, but not limited to, germs, and/or accidental touch. Piercing element 41 has at least one opening 43 connected to conduit 44. When an end of medicine vial 34 is depressed within loading chamber 35, the end of medicine vial 34 is punctured by second piercing element 41. The fluid and/or substance retained within medicine vial 34 flows through at least one opening 43 of second piercing element 41 and continues to flow through conduit 44 into barrel 9 of syringe 10. Conduit 44 traverses through the length of sealing structure 17 so that fluids flow through opening 43 of second piercing element 41 and through conduit 44 to allow medicines, air, and/or other fluid to flow between medicine vial 34 and barrel 9 of syringe 10. It is within the scope of this invention for secondary piercing element 41 to pierce a medical vial 34 along with the protruding structure 37 of loading chamber 35 and conduit 44 can be relocated anywhere within plunger 18. This modification will allow larger medical vials to be used.

FIG. 6 shows secondary piercing element 41 having a plurality of openings 43A-43C. Medical vial 34 has barcode 45. Plunger 18 and its components have been inserted into barrel 9 of syringe 10. It is within the scope of the invention that one or more mechanisms including, but not limited to, recapping, twisting 46, pushing, and/or pulling with or without using pressure-controlled valve(s) may be used to control the flow of fluid in and out of barrel 9 of syringe 10. An example of twisting 46 plunger 18 to orient conduit 77 in an opened configuration 47 by positioning conduit 44 aligned over opening 49 for mixing and to a closed configuration 48 by repositioning it under another part of sealing structure 17 without an opening. Referring now to FIGS. 5-7, sealing structure 17 has opening 49 that allows conduit 44, that when oriented in open configuration 47, the fluid from a medicine vial 34 may flow from the medicine vial 34 through openings 43A-43C of second piercing element 41, through conduit 44 traversing through sealing structure 17, and exiting into barrel 9 of syringe 10. As best shown in FIGS. 6 and 8, it is within the scope of this current invention for second piercing element 41 to have at least one wing 50A and 50B configured to puncture medicine vial 34.

FIG. 8 shows a fourth embodiment of sealing structure 53 of the third embodiment where sealing structure 53 has first cylindrical structure 51 located above second cylindrical structure 52. Sealing structure 53 is located at the stopper end of plunger 18 of syringe 10. First cylindrical structure 51 has at least one bore 54. It is within the scope of this invention for first cylindrical structure 51 having first bore 54A and second bore 54B. Second cylindrical structure 52 has at least one bore 54. It is within the scope of this invention for second cylindrical structure 55 having third bore 54C and fourth bore 54D. Sealing structure 53 is configured to allow the exchange of materials such as fluid expelled from medicine vial 34 from plunger 18 portion of syringe 10 to barrel portion 9 of syringe 10. First bore 54A and second bore 54B of first cylindrical structure may be oriented in an open configuration to align 47 with third bore 54C and fourth bore 54D, respectively, to facilitate flow of fluid from plunger 18 to barrel 9 of syringe 10. A closed orientation 48 is when second sealing structure 53 is turned and bore 54E of first cylindrical structure 51 and bore 54F of second cylindrical structure 52 do not align. In closed orientation 48, the exchange between content of plunger 18 and barrel 8 of syringe 10 is restricted. Second piercing element 41 having at least one opening 43A-43C is connected to first cylindrical structure 51. Second piercing element 41 can have wings 50A and 50B which are configured to engage an end of medicine vial 34, whereby, when medicine vial 34 is turned by a user, the first cylinder structure 51 of sealing structure 53 twists because it is movable. First cylinder 51 of sealing structure 53 may be oriented and/or twisted in either an open 47 or closed 48 configuration to align with openings of second cylinder structure 52. First piercing element 14 is connected to second cylindrical structure 52.

In another embodiment, a clamp could be located below plurality of support structure ribs 36. The clamp is configured to open or close the access of fluid and/or substance flow between plunger portion and barrel portion of the syringe.

Figure 9:
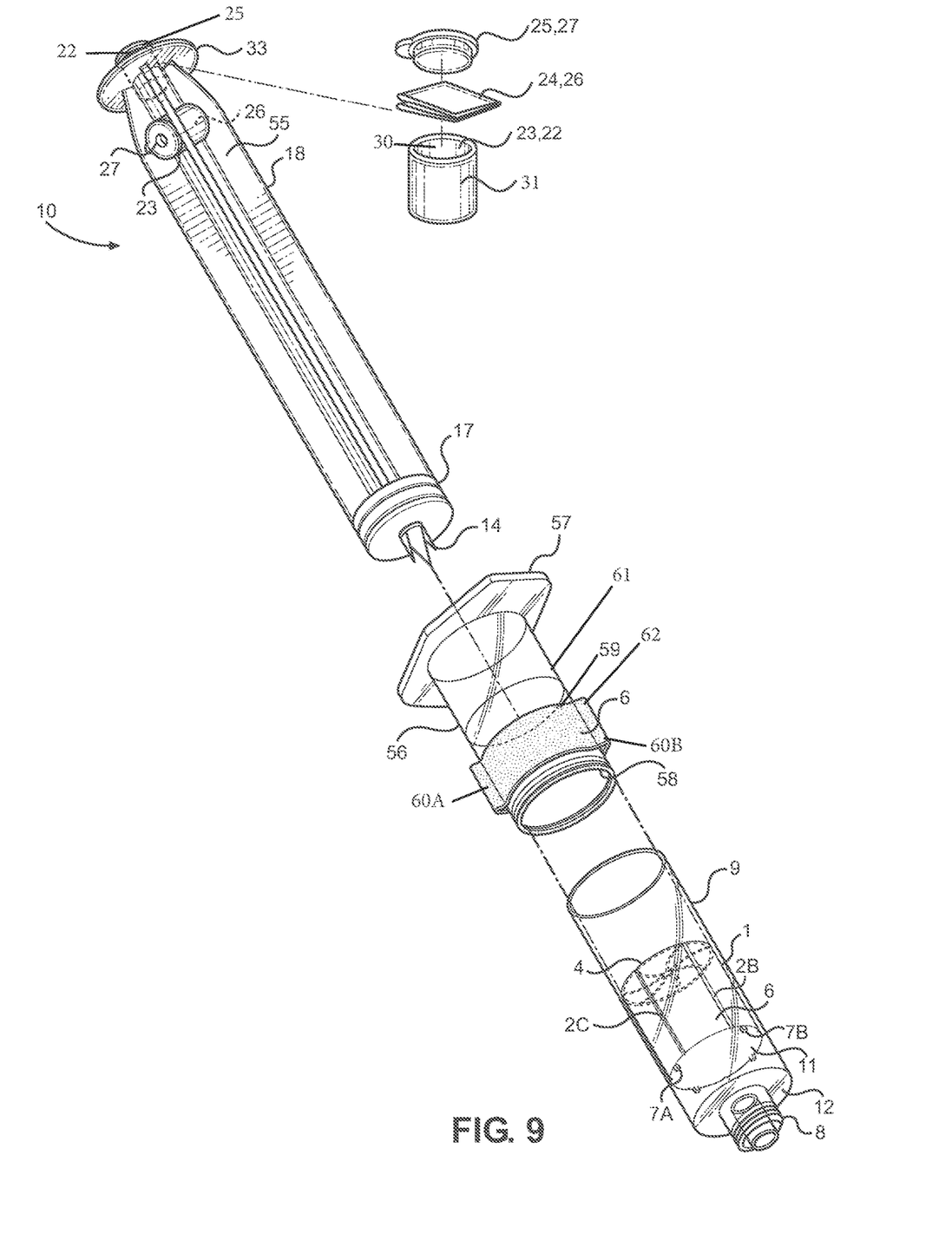

FIG. 9 illustrates a fifth embodiment being the syringe 10 of FIG. 4, having a second barrel 56 having flange 57 and retaining solution 6 within vessel 59. It is within the scope of this invention for vessel 59 to include a second container such as a medicine vial having flange 57 and/or to be integrally formed within second barrel 56. Vessel 59 can have at least a portion of outer wall surface of vessel 59 having first diameter 61 and second diameter 62. First diameter 61 is smaller in size than second diameter 62. Second diameter 62 may include at least one of first wing 60A and/or second wing 60B. Vessel 59 may be collapsible and/or deformable when the force of plunger 19 is depressed against vessel 59. The force of a plunger 19 and/or the force of vessel 59 may include, but not be limited to, a user depressing, traversing, or twisting. Vessel 59 may be a rigid container that can have at least a portion that can be punctured by piercing element 14 of plunger 19. Seal 58 of second barrel 56 may be positioned at including, but not limited to, an end of barrel 56 or seal 58 may be placed at an end of first barrel 9. Vessel 59 may have an end having a piercing element configured to pierce a first collapsible container. The modification of FIG. 9 shows medical container or vial 59 in which it is located above first barrel 9 of syringe 10 and is positioned directly below plunger 19 having plunger seal 17 and first piercing element 14. It is within the scope of this invention for vessel 59 to be removable and/or be attached permanently to the syringe barrel. A second puncture mechanism could be added to vessel 59 but is not necessary. The larger diameter 62 is there but is not a necessary feature for the fix or removable medical vial to work.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

The invention claimed is:

1. A syringe, comprising:
a plunger having a shaft, said shaft of said plunger having a flange located opposite a sealing structure, said sealing structure having a first side located opposite a second side, said first side of said sealing structure having a first piercing element, said second side of said sealing structure connected to said shaft of said plunger;
a barrel, said barrel having a chamber receiving said sealing structure of said plunger; and,
a first container, said first container is retained within said barrel, said first container retaining a substance, said first container is configured to be punctured by said first piercing element when a user depresses said plunger within said barrel of said syringe;
wherein said first container includes at least one longitudinal channel located on an outer wall surface of said first container to allow for the substance to move along the outer surface from a proximal end to a distal end of the first container.

2. The syringe of claim 1, wherein said first container is collapsible.

3. The syringe of claim 1, wherein said plunger having at least one recess retaining an alcohol pad.

4. The syringe of claim 3, wherein said at least one recess of said plunger having a removable lid.

5. The syringe of claim 1, wherein said barrel of said syringe retaining a second container, said second container retaining a substance, said second container is configured to be punctured by said first piercing element when a user depresses said plunger within said barrel of said syringe.

6. The syringe of claim 1, wherein said shaft of said plunger having a loading chamber, said loading chamber receiving a vessel retaining a substance.

7. The syringe of claim 6, wherein said loading chamber of said plunger having an inner wall surface having at least one protruding structure, said at least one protruding structure is configured to engage said vessel and secure said vessel within said loading chamber.

8. The syringe of claim 6, wherein said second side of said sealing structure having at least one support structure, said at least one support structure is configured to engage said vessel and secure said vessel within said loading chamber.

9. The syringe of claim 6, wherein said second side of said sealing structure having a second piercing element, said second piercing element is configured to puncture at least a portion of said vessel to release said substance from said vessel when a user depresses said vessel into said loading chamber of said plunger, said second piercing element having at least one opening, said at least one opening of said second piercing element is connected to a conduit, said conduit traversing through said sealing structure of said plunger to said barrel of said syringe, said conduit is configured to be oriented in a closed orientation to prevent said substance from flowing from said plunger to said barrel of said syringe, said conduit is configured to be oriented in an open orientation to allow said substance to flow from said plunger to said barrel of said syringe.

10. The syringe of claim 9, wherein said second piercing element having at least one flange.

11. The syringe of claim 6, wherein said sealing structure having a first cylindrical structure having a first bore and a second bore, said sealing structure having a second cylindrical structure having a third bore and a fourth bore, said second side of said sealing structure having a second piercing element, said second piercing element configured to puncture at least a portion of said vessel to release said substance from said vessel when a user depresses said vessel into said loading chamber of said plunger, said second piercing element having at least one opening, said at least one opening of said second piercing element is connected to said first bore and said second bore of said first cylindrical structure, said first bore and said second bore of said first cylindrical structure are oriented in an open configuration to align with said third bore and said fourth bore of said second cylindrical structure to allow said substance to flow from said vessel of said plunger to said barrel of said syringe.

12. The syringe of claim 11, wherein said second piercing element having at least one flange.

13. A syringe, comprising:
- a plunger having a shaft, said shaft of said plunger having a flange located opposite a sealing structure, said sealing structure having a first side located opposite a second side, said first side of said sealing structure having a first piercing element, said second side of said sealing structure connected to said shaft of said plunger;
- a barrel, said barrel having a chamber receiving said sealing structure of said plunger;
- a first container, said first container is retained within said barrel, said first container retaining a substance, said first container is configured to be punctured by said first piercing element when a user depresses said plunger within said barrel of said syringe;
- wherein said first container includes at least one longitudinal channel located on an outer wall surface of said first container to allow for the substance to move along the outer surface from a proximal end to a distal end of the first container; and,
- a second container, said barrel of said syringe retaining at least a portion of said second container, said second container retaining a substance, said second container is configured to be punctured by said first piercing element when a user depresses said plunger within said barrel of said syringe.

14. The syringe of claim 13, wherein said first container is collapsible.

15. The syringe of claim 13, wherein said plunger having at least one recess retaining an alcohol pad.

16. The syringe of claim 15, wherein said at least one recess of said plunger having a removable lid.

17. The syringe of claim 13, wherein said second container having a flange, said flange is connected to an end of said second container.

18. The syringe of claim 13, wherein said second container having a first diameter and a second diameter, said second diameter is greater in size than said first diameter.

\* \* \* \* \*